(12) United States Patent
O'Brien et al.

(10) Patent No.: US 11,998,686 B2
(45) Date of Patent: Jun. 4, 2024

(54) CONTAINED LIQUID SYSTEM FOR REFILLING AEROSOL DELIVERY DEVICES

(71) Applicant: RAI Strategic Holdings, Inc., Winston-Salem, NC (US)

(72) Inventors: John Brice O'Brien, Winston-Salem, NC (US); Frederic Philippe Ampolini, Winston-Salem, NC (US); James William Rogers, Winston-Salem, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 0 days.

(21) Appl. No.: 17/962,759

(22) Filed: Oct. 10, 2022

(65) Prior Publication Data

US 2023/0033123 A1 Feb. 2, 2023

Related U.S. Application Data

(62) Division of application No. 14/802,667, filed on Jul. 17, 2015, now Pat. No. 11,504,489.

(51) Int. Cl.
*A61M 15/06* (2006.01)
*A24F 15/015* (2020.01)
(Continued)

(52) U.S. Cl.
CPC .......... *A61M 15/06* (2013.01); *A24F 40/485* (2020.01); *A61M 11/042* (2014.02); *B65B 3/04* (2013.01);
(Continued)

(58) Field of Classification Search
CPC .... A24F 47/008; A24F 40/485; A24F 15/015; A61M 11/042; A61M 15/06; A61M 2209/045; B65B 3/04; B65B 31/00
(Continued)

(56) References Cited

U.S. PATENT DOCUMENTS

| 1,771,366 A | 7/1930 | Wyss et al. |
| 2,057,353 A | 10/1936 | Whittemore, Jr. |

(Continued)

FOREIGN PATENT DOCUMENTS

| AU | 276250 | 7/1965 |
| CA | 2 641 869 | 5/2010 |

(Continued)

OTHER PUBLICATIONS

Extended European Search Report from the corresponding European Patent Application No. 20177767.9, dated Oct. 2, 2020.
(Continued)

*Primary Examiner* — Nathaniel E Wiehe
*Assistant Examiner* — Alba T Rosario-Aponte
(74) *Attorney, Agent, or Firm* — Womble Bond Dickinson (US) LLP

(57) ABSTRACT

A contained liquid system for use with a refillable aerosol delivery device is provided. The contained liquid system includes an aerosol delivery device having an adapter therein for receiving aerosol precursor composition within a reservoir of the aerosol delivery device, and a container of aerosol precursor composition having a corresponding adapter therein for transferring aerosol precursor composition from the container. The adapter and the corresponding adapter are removably, sealably connectable for refilling the aerosol delivery device with aerosol precursor composition. The adapter engages a valve of the corresponding adapter and includes a body defining separate and distinct filling airflow ports. The filling port transfers aerosol precursor composition from the container into the aerosol delivery device. The airflow port enables a flow of air through at least the portion of the aerosol delivery device when the adapter and valve are disengaged.

11 Claims, 13 Drawing Sheets

(51) Int. Cl.
  *A24F 40/10* (2020.01)
  *A24F 40/485* (2020.01)
  *A61M 11/04* (2006.01)
  *B65B 3/04* (2006.01)
  *B65B 31/00* (2006.01)

(52) U.S. Cl.
  CPC ............ *B65B 31/00* (2013.01); *A24F 15/015* (2020.01); *A24F 40/10* (2020.01); *A61M 2209/045* (2013.01)

(58) Field of Classification Search
  USPC ................................ 392/404, 403, 394, 386
  See application file for complete search history.

(56) References Cited

U.S. PATENT DOCUMENTS

| | | |
|---|---|---|
| 2,104,266 A | 1/1938 | McCormick |
| 3,200,819 A | 8/1965 | Gilbert |
| 4,284,089 A | 8/1981 | Ray |
| 4,303,083 A | 12/1981 | Burruss, Jr. |
| 4,735,217 A | 4/1988 | Gerth et al. |
| 4,848,374 A | 7/1989 | Chard et al. |
| 4,907,606 A | 3/1990 | Lilja et al. |
| 4,922,901 A | 5/1990 | Brooks et al. |
| 4,945,931 A | 8/1990 | Gori |
| 4,947,874 A | 8/1990 | Brooks et al. |
| 4,947,875 A | 8/1990 | Brooks et al. |
| 4,986,286 A | 1/1991 | Roberts et al. |
| 5,019,122 A | 5/1991 | Clearman et al. |
| 5,042,510 A | 8/1991 | Curtiss et al. |
| 5,060,671 A | 10/1991 | Counts et al. |
| 5,093,894 A | 3/1992 | Deevi et al. |
| 5,144,962 A | 9/1992 | Counts et al. |
| 5,249,586 A | 10/1993 | Morgan et al. |
| 5,261,424 A | 11/1993 | Sprinkel, Jr. |
| 5,322,075 A | 6/1994 | Deevi et al. |
| 5,353,813 A | 10/1994 | Deevi et al. |
| 5,369,723 A | 11/1994 | Counts et al. |
| 5,372,148 A | 12/1994 | McCafferty et al. |
| 5,388,574 A | 2/1995 | Ingebrethsen et al. |
| 5,408,574 A | 4/1995 | Deevi et al. |
| 5,468,936 A | 11/1995 | Deevi et al. |
| 5,498,850 A | 3/1996 | Das |
| 5,515,842 A | 5/1996 | Ramseyer et al. |
| 5,530,225 A | 6/1996 | Hajaligol |
| 5,564,442 A | 10/1996 | MacDonald et al. |
| 5,649,554 A | 7/1997 | Sprinkel et al. |
| 5,666,977 A | 9/1997 | Higgins et al. |
| 5,687,746 A | 11/1997 | Rose et al. |
| 5,726,421 A | 3/1998 | Fleischhauer et al. |
| 5,727,571 A | 3/1998 | Meiring et al. |
| 5,743,251 A | 4/1998 | Howell et al. |
| 5,799,663 A | 9/1998 | Gross et al. |
| 5,819,756 A | 10/1998 | Mielordt |
| 5,865,185 A | 2/1999 | Collins et al. |
| 5,865,186 A | 2/1999 | Volsey, II |
| 5,878,752 A | 3/1999 | Adams et al. |
| 5,894,841 A | 4/1999 | Voges |
| 5,934,289 A | 8/1999 | Watkins et al. |
| 5,954,979 A | 9/1999 | Counts et al. |
| 5,967,148 A | 10/1999 | Harris et al. |
| 6,040,560 A | 3/2000 | Fleischhauer et al. |
| 6,053,176 A | 4/2000 | Adams et al. |
| 6,089,857 A | 7/2000 | Matsuura et al. |
| 6,095,153 A | 8/2000 | Kessler et al. |
| 6,125,853 A | 10/2000 | Susa et al. |
| 6,155,268 A | 12/2000 | Takeuchi |
| 6,164,287 A | 12/2000 | White |
| 6,196,218 B1 | 3/2001 | Voges |
| 6,196,219 B1 | 3/2001 | Hess et al. |
| 6,598,607 B2 | 7/2003 | Adiga et al. |
| 6,601,776 B1 | 8/2003 | Oljaca et al. |
| 6,615,840 B1 | 9/2003 | Fournier et al. |
| 6,688,313 B2 | 2/2004 | Wrenn et al. |
| 6,772,756 B2 | 8/2004 | Shayan |
| 6,803,545 B2 | 10/2004 | Blake et al. |
| 6,854,461 B2 | 2/2005 | Nichols |
| 6,854,470 B1 | 2/2005 | Pu |
| 7,086,431 B2 | 8/2006 | D'Antonio et al. |
| 7,117,867 B2 | 10/2006 | Cox et al. |
| 7,293,565 B2 | 11/2007 | Griffin et al. |
| 7,513,253 B2 | 4/2009 | Kobayashi et al. |
| 7,775,459 B2 | 8/2010 | Martens, III et al. |
| 7,832,410 B2 | 11/2010 | Hon |
| 7,845,359 B2 | 12/2010 | Montaser |
| 7,896,006 B2 | 3/2011 | Hamano et al. |
| 8,127,772 B2 | 3/2012 | Montaser |
| 8,314,591 B2 | 11/2012 | Terry et al. |
| 8,365,742 B2 | 2/2013 | Hon |
| 8,402,976 B2 | 3/2013 | Fernando et al. |
| 8,499,766 B1 | 8/2013 | Newton |
| 8,505,548 B2 | 8/2013 | Hearn |
| 8,528,569 B1 | 9/2013 | Newton |
| 8,550,069 B2 | 10/2013 | Alelov |
| 8,757,169 B2 | 6/2014 | Gysland |
| 8,910,639 B2 | 12/2014 | Chang et al. |
| 9,022,039 B2 | 5/2015 | Hearn |
| 9,717,276 B2 | 8/2017 | Brammer et al. |
| 9,763,474 B2 | 9/2017 | Hearn |
| 9,839,237 B2 | 12/2017 | Chang et al. |
| 2002/0146242 A1 | 10/2002 | Vieira |
| 2003/0226837 A1 | 12/2003 | Blake et al. |
| 2004/0118401 A1 | 6/2004 | Smith et al. |
| 2004/0129280 A1 | 7/2004 | Woodson et al. |
| 2004/0200488 A1 | 10/2004 | Felter et al. |
| 2004/0226568 A1 | 11/2004 | Takeuchi et al. |
| 2005/0016550 A1 | 1/2005 | Katase |
| 2006/0016453 A1 | 1/2006 | Kim |
| 2006/0196518 A1 | 9/2006 | Hon |
| 2007/0074734 A1 | 4/2007 | Braunshteyn et al. |
| 2007/0102013 A1 | 5/2007 | Adams et al. |
| 2007/0215167 A1 | 9/2007 | Crooks et al. |
| 2007/0267031 A1 | 11/2007 | Hon |
| 2008/0085103 A1 | 4/2008 | Beland et al. |
| 2008/0092912 A1 | 4/2008 | Robinson et al. |
| 2008/0257367 A1 | 10/2008 | Paterno et al. |
| 2008/0276947 A1 | 11/2008 | Martzel |
| 2008/0302374 A1 | 12/2008 | Wengert et al. |
| 2009/0095311 A1 | 4/2009 | Hon |
| 2009/0095312 A1 | 4/2009 | Herbrich et al. |
| 2009/0126745 A1 | 5/2009 | Hon |
| 2009/0188490 A1 | 7/2009 | Hon |
| 2009/0230117 A1 | 9/2009 | Fernando et al. |
| 2009/0255534 A1 | 10/2009 | Paterno |
| 2009/0272379 A1 | 11/2009 | Thorens et al. |
| 2009/0283103 A1 | 11/2009 | Nielsen et al. |
| 2009/0320863 A1 | 12/2009 | Fernando et al. |
| 2010/0043809 A1 | 2/2010 | Magnon |
| 2010/0083959 A1 | 4/2010 | Siller |
| 2010/0200006 A1 | 8/2010 | Robinson et al. |
| 2010/0229881 A1 | 9/2010 | Hearn |
| 2010/0242974 A1 | 9/2010 | Pan |
| 2010/0307518 A1 | 12/2010 | Wang |
| 2010/0313901 A1 | 12/2010 | Fernando et al. |
| 2011/0005535 A1 | 1/2011 | Xiu |
| 2011/0011396 A1 | 1/2011 | Fang |
| 2011/0036363 A1 | 2/2011 | Urtsev et al. |
| 2011/0036365 A1 | 2/2011 | Chong et al. |
| 2011/0087164 A1 | 4/2011 | Mosler et al. |
| 2011/0094523 A1 | 4/2011 | Thorens et al. |
| 2011/0126848 A1 | 6/2011 | Zuber et al. |
| 2011/0155153 A1 | 6/2011 | Thorens et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0309157 A1 | 12/2011 | Yang et al. |
| 2011/0315152 A1 | 12/2011 | Hearn et al. |
| 2012/0042885 A1 | 2/2012 | Stone et al. |
| 2012/0060853 A1 | 3/2012 | Robinson et al. |
| 2012/0111347 A1 | 5/2012 | Hon |
| 2012/0132643 A1 | 5/2012 | Choi et al. |
| 2012/0167906 A1 | 7/2012 | Gysland |
| 2012/0227752 A1 | 9/2012 | Alelov |

(56) References Cited

U.S. PATENT DOCUMENTS

| | | |
|---|---|---|
| 2012/0231464 A1 | 9/2012 | Yu et al. |
| 2012/0260927 A1 | 10/2012 | Liu |
| 2012/0279512 A1 | 11/2012 | Hon |
| 2012/0285476 A1 | 11/2012 | Hon |
| 2012/0318283 A1 | 12/2012 | Watanabe et al. |
| 2012/0318882 A1 | 12/2012 | Abehasera |
| 2013/0037041 A1 | 2/2013 | Worm et al. |
| 2013/0037042 A1 | 2/2013 | Hearn et al. |
| 2013/0056013 A1 | 3/2013 | Terry et al. |
| 2013/0081625 A1 | 4/2013 | Rustad et al. |
| 2013/0081642 A1 | 4/2013 | Safari |
| 2013/0087160 A1 | 4/2013 | Gherghe |
| 2013/0192618 A1 | 8/2013 | Li et al. |
| 2013/0192619 A1 | 8/2013 | Tucker et al. |
| 2013/0213420 A1 | 8/2013 | Hon |
| 2013/0255702 A1 | 10/2013 | Griffith, Jr. et al. |
| 2013/0269684 A1 | 10/2013 | Patton |
| 2013/0306084 A1 | 11/2013 | Flick |
| 2013/0319439 A1 | 12/2013 | Gorelick et al. |
| 2013/0340750 A1 | 12/2013 | Thorens et al. |
| 2013/0340775 A1 | 12/2013 | Juster et al. |
| 2014/0000638 A1 | 1/2014 | Sebastian et al. |
| 2014/0060554 A1 | 3/2014 | Collett et al. |
| 2014/0060555 A1 | 3/2014 | Chang et al. |
| 2014/0076310 A1 | 3/2014 | Newton |
| 2014/0096781 A1 | 4/2014 | Sears et al. |
| 2014/0096782 A1 | 4/2014 | Ampolini et al. |
| 2014/0109921 A1 | 4/2014 | Chen |
| 2014/0123989 A1 | 5/2014 | LaMothe |
| 2014/0157583 A1 | 6/2014 | Ward et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0345631 A1 | 11/2014 | Bowen et al. |
| 2015/0053217 A1 | 2/2015 | Steingraber et al. |
| 2015/0097513 A1 | 4/2015 | Liberti et al. |
| 2015/0117841 A1 | 4/2015 | Brammer et al. |
| 2015/0128974 A1 | 5/2015 | Hon |
| 2015/0144145 A1 | 5/2015 | Chang et al. |
| 2015/0231108 A1 | 8/2015 | Hearn et al. |
| 2015/0245654 A1* | 9/2015 | Memari .............. H05K 999/00 141/2 |
| 2016/0120227 A1* | 5/2016 | Levitz .................... F16K 1/221 141/2 |
| 2016/0128384 A1 | 5/2016 | Luciani |
| 2016/0332754 A1* | 11/2016 | Brown .................. B65B 3/10 |
| 2016/0345630 A1 | 12/2016 | Mironov et al. |
| 2018/0027874 A1* | 2/2018 | Zhu ...................... H05B 3/03 |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| CN | 104738816 | 7/2015 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 1 736 065 | 12/2006 |
| EP | 2 316 286 | 5/2011 |
| EP | 2 792 256 | 10/2014 |
| EP | 3 123 879 | 2/2017 |
| GB | 2469850 | 11/2010 |
| JP | 2006-512114 | 4/2006 |
| JP | 2010-531186 | 9/2010 |
| KR | 10-2015-0009908 | 1/2015 |
| UA | 112105 | 7/2016 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | WO 2005/099494 | 10/2005 |
| WO | WO 2007/078273 | 7/2007 |
| WO | WO 2007/131449 | 11/2007 |
| WO | WO 2009/001082 | 12/2008 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | WO 2011/104829 | 9/2011 |
| WO | WO 2012/072762 | 6/2012 |
| WO | WO 2012/100523 | 8/2012 |
| WO | WO 2013/089551 | 6/2013 |
| WO | WO 2013/111320 | 8/2013 |
| WO | WO 2014/033438 | 3/2014 |
| WO | WO 2014/155089 | 10/2014 |
| WO | WO 2014/155090 | 10/2014 |
| WO | WO 2014/155092 | 10/2014 |
| WO | WO 2014/155095 | 10/2014 |
| WO | WO 2014/199098 | 12/2014 |

OTHER PUBLICATIONS

International Search Report for International Application PCT/US2016/042039 dated Oct. 11, 2016.

\* cited by examiner

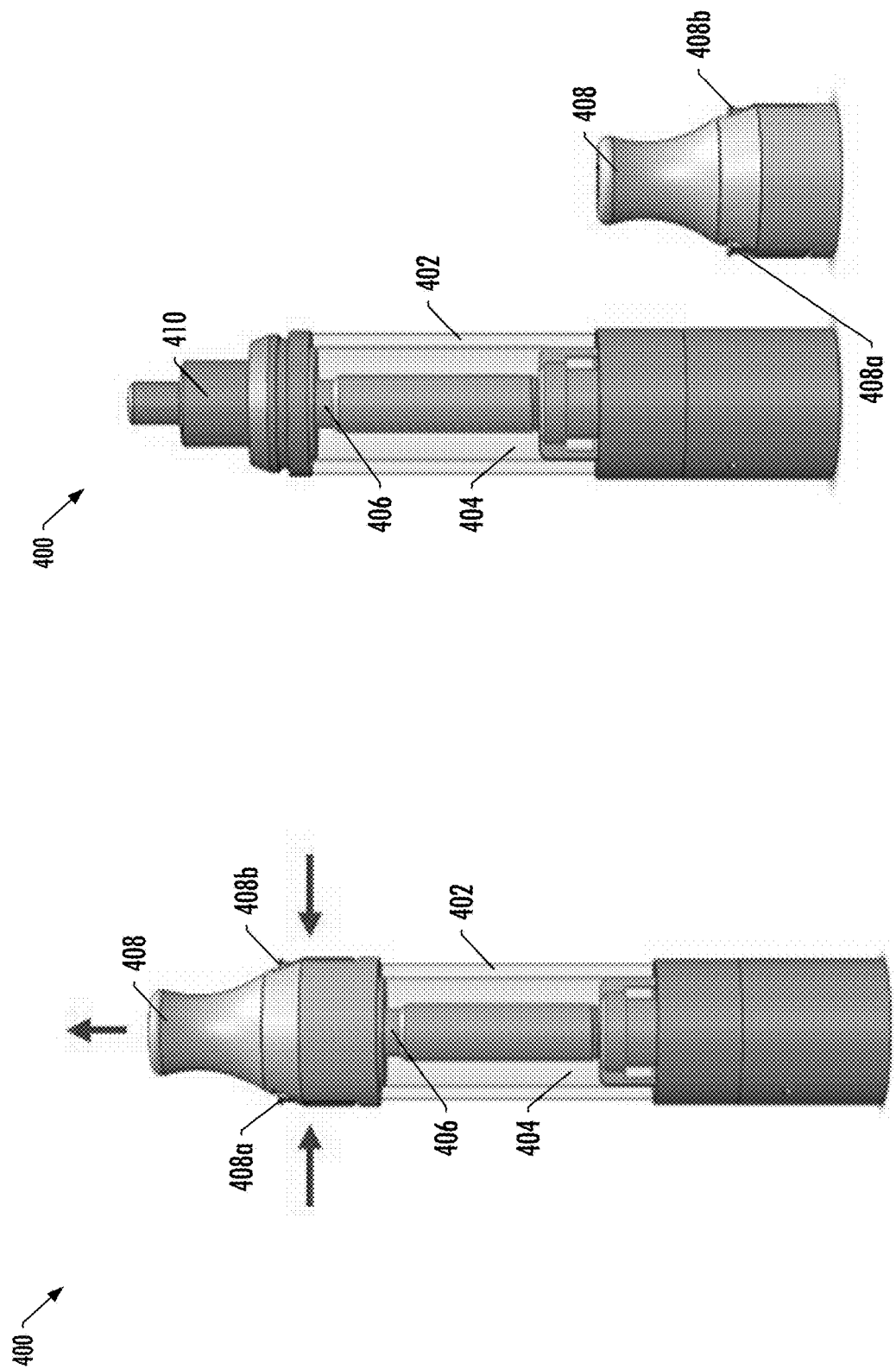

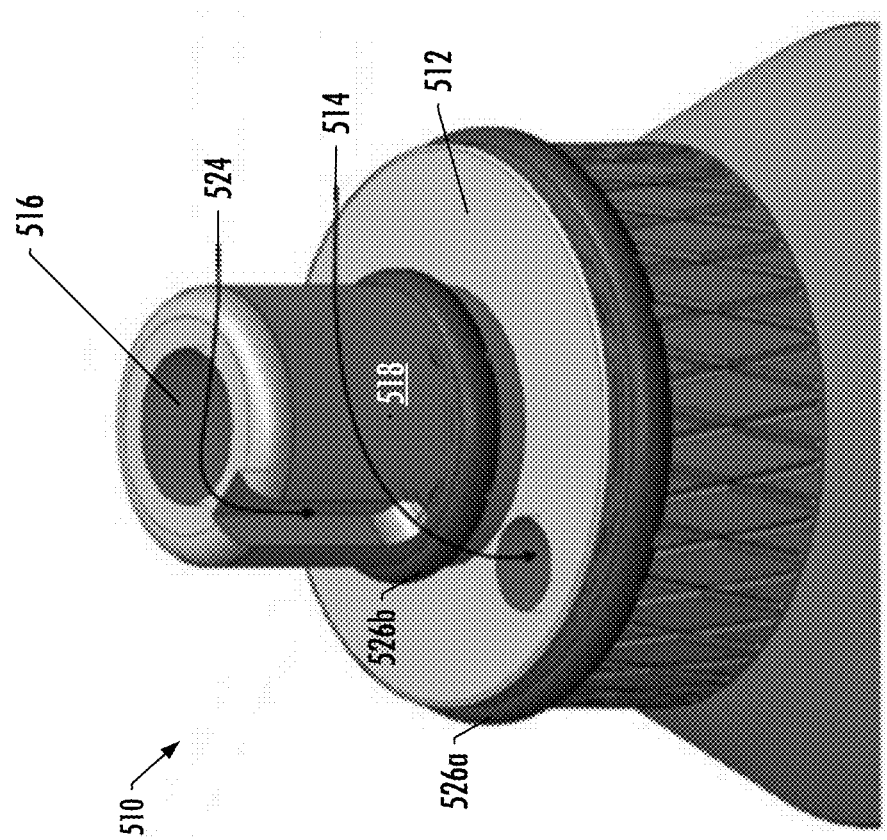
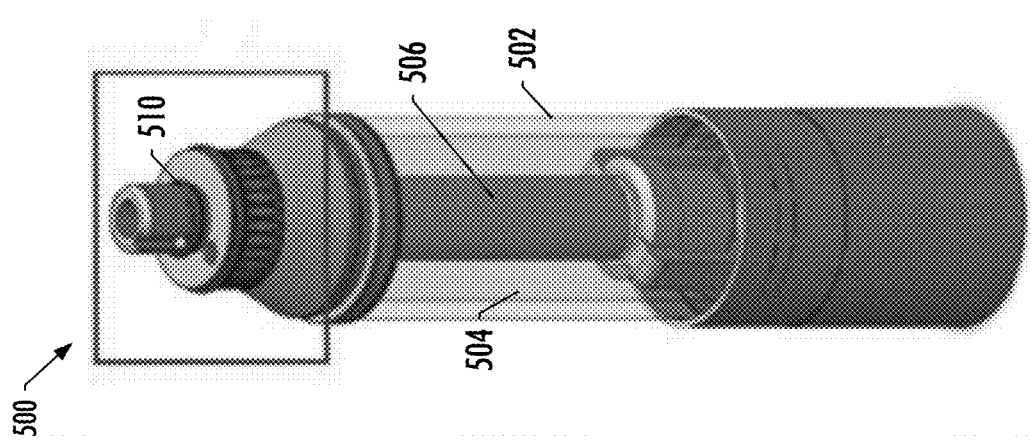
FIG. 5B
FIG. 5A

```
                    ┌─────────┐
                    │  START  │
                    └────┬────┘
                         ▼
┌─────────────────────────────────────────────────────────────────┐
│ REMOVABLY, SEALABLY CONNECTING AN ADAPTER OF AN AEROSOL         │
│ DELIVERY DEVICE WITH A CORRESPONDING ADAPTER OF A CONTAINER FOR │
│ REFILLING THE AEROSOL DELIVERY DEVICE WITH AEROSOL PRECURSOR    │
│ COMPOSITION                                                      │
│                              1402                                │
└─────────────────────────────┬───────────────────────────────────┘
                              ▼
┌─────────────────────────────────────────────────────────────────┐
│ TRANSFERRING AEROSOL PRECURSOR COMPOSITION FROM THE CONTAINER    │
│ INTO THE AEROSOL DELIVERY DEVICE                                 │
│                              1404                                │
└─────────────────────────────┬───────────────────────────────────┘
                              ▼
                    ┌─────────┐
                    │   END   │
                    └─────────┘
```

FIG. 14

CONTAINED LIQUID SYSTEM FOR REFILLING AEROSOL DELIVERY DEVICES

CROSS-REFERENCE TO RELATED APPLICATION(S)

This application is a division of U.S. patent application Ser. No. 14/802,667, filed Jul. 17, 2015, entitled CONTAINED LIQUID SYSTEM FOR REFILLING AEROSOL DELIVERY DEVICES, the content of which is incorporated herein in its entirety by reference.

TECHNOLOGICAL FIELD

The present disclosure relates to aerosol delivery devices such as smoking articles that may utilize electrically generated heat for the production of aerosol (e.g., smoking articles commonly referred to as electronic cigarettes), and more particularly to a system and method for safely refilling aerosol delivery devices with an aerosol precursor composition. The smoking articles may be configured to heat the aerosol precursor, which may incorporate materials that may be made or derived from tobacco or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar or pipe smoking, but without delivering considerable quantities of incomplete combustion and pyrolysis products that result from the burning of tobacco. To this end, there have been proposed numerous smoking products, flavor generators and medicinal inhalers that utilize electrical energy to vaporize or heat a volatile material, or attempt to provide the sensations of cigarette, cigar or pipe smoking without burning tobacco to a significant degree. See, for example, the various alternative smoking articles, aerosol delivery devices and heat generating sources set forth in the background art described in U.S. Pat. No. 7,726,320 to Robinson et al., U.S. Pat. App. Pub. No. 2013/0255702 to Griffith Jr. et al., and U.S. Pat. App. Pub. No. 2014/0096781 to Sears et al., all of which are incorporated herein by reference in their entireties. See also, for example, the various types of smoking articles, aerosol delivery devices and electrically-powered heat generating sources referenced by brand name and commercial source in U.S. patent application Ser. No. 14/170,838 to Bless et al., filed Feb. 3, 2014, which is incorporated herein by reference in its entirety. Additionally, other types of smoking articles have been proposed in U.S. Pat. No. 5,505,214 to Collins et al., U.S. Pat. No. 5,894,841 to Voges, U.S. Pat. No. 6,772,756 to Shayan, U.S. Pat. App. Pub. No. 2006/0196518 to Hon, U.S. Pat. App. Pub. No. 2007/0267031 to Hon, and U.S. patent application Ser. No. 14/716,204 to Minskoff et al., all of which are incorporated herein by reference in their entireties.

Ongoing developments in the field of aerosol delivery devices have resulted in providing refillable reservoirs for use with containing an aerosol precursor composition in an aerosol delivery device, the refillable reservoir being configured such that the aerosol delivery devices are reusable. However, refilling such reservoirs can often lead to hazardous user-exposure to the aerosol precursor composition. Therefore, a need exist for a system and method for safely refilling aerosol delivery devices with an aerosol precursor composition.

SUMMARY OF THE DISCLOSURE

The present disclosure relates to aerosol delivery devices, methods of forming such devices, and elements of such devices. The present disclosure thus includes, without limitation, the following example implementations. In some example implementations, an aerosol delivery device is provided that includes a housing coupled to an adapter, and a heating element contained within the housing. The housing defines a refillable reservoir for storing an aerosol precursor composition. The heating element is configured to activate and vaporize components of the aerosol precursor composition in response to a flow of air through at least a portion of the housing, the air being combinable with a thereby formed vapor to form an aerosol. The adapter may be removably, sealably connectable with a container for refilling the reservoir with aerosol precursor composition. The adapter may be configured to engage a valve of the container during refilling of the reservoir. The adapter may include a body defining separate and distinct filling and airflow ports. The filling port being for transfer of aerosol precursor composition from the container into the reservoir during engagement of the adapter and valve in which the airflow port is closed by the valve to prevent the aerosol precursor composition from passing through the airflow port. The airflow port may be for the flow of air through at least the portion of the housing when the adapter and valve are disengaged.

In some example implementations of the aerosol delivery device of the preceding or any subsequent example implementation, or any combination thereof, the valve includes a depressible valve body including a first valve member and a second valve member, the first valve member being for opening a passageway to aerosol precursor composition within the container, and the second valve member being for closing the airflow port, when the valve body is depressed.

In some example implementations of the aerosol delivery device of any preceding or any subsequent example implementation, or any combination thereof, the airflow port defines an inner cavity sized to receive therein at least a matching portion of the second valve member.

In some example implementations, the body includes an adapter protrusion defining the airflow port, and the container includes a nozzle within which the valve is movably positioned, the nozzle including a cavity sized to receive therein the at least portion of the valve when the adapter and valve are disengaged, and the adapter protrusion when the adapter and valve are engaged.

In some example implementations of the aerosol delivery device of any preceding or any subsequent example implementation, or any combination thereof, the nozzle includes a spout for transfer of aerosol precursor composition from the container into the reservoir, and the filling port is sized to receive the spout when the adapter and valve are engaged.

In some example implementations of the aerosol delivery device of any preceding or any subsequent example implementation, or any combination thereof, the adapter further includes a check valve coupled to the filling port and configured to allow the transfer of aerosol precursor composition from the container into the reservoir.

In some example implementations of the aerosol delivery device of any preceding or any subsequent example implementation, or any combination thereof, the aerosol delivery device further comprises a mouthpiece removably coupled to the housing over the adapter such that the adapter is exposed upon removal of the mouthpiece.

In some example implementations of the aerosol delivery device of any preceding or any subsequent example implementation, or any combination thereof, the mouthpiece is a removal-resistant mouthpiece including two tabs the simultaneous pressing of which allows the removal-resistant mouthpiece to turn and thereby release from the housing.

In some example implementations of the aerosol delivery device of any preceding or any subsequent example implementation, or any combination thereof, the adapter further includes a slot mateable with a matching tab of the container to align the adapter with the container for connection therewith.

In some example implementations, a container of aerosol precursor composition for refilling aerosol delivery devices is provided. The container includes a housing defining a reservoir for storing an aerosol precursor composition, and an adapter coupled to the housing. The adapter may be removably, sealably connectable with an aerosol delivery device to enable refilling the aerosol delivery device with aerosol precursor composition. The adapter may include a valve configured to engage the aerosol delivery device during refilling of the aerosol delivery device.

In some example implementations of the container of the preceding or any subsequent example implementation, or any combination thereof, the nozzle defines one or more liquid ports configured to allow the transfer of aerosol precursor composition from the reservoir into the aerosol delivery device.

In some example implementations of the container of any preceding or any subsequent example implementation, or any combination thereof, the container further comprises a cap removably coupled to the housing over the adapter such that the adapter is exposed upon removal of the cap.

In some example implementations of the container of any preceding or any subsequent example implementation, or any combination thereof, the cap is a removal-resistant cap including two tabs the simultaneous pressing of which allows the removal-resistant cap to turn and thereby its removal from the housing.

In some example implementations of the container of any preceding or any subsequent example implementation, or any combination thereof, the adapter further includes a tab mateable with a matching slot of the aerosol delivery device to align the adapter with the aerosol delivery device for connection therewith.

In some example implementations, a method for implementing a contained liquid system for use with a refillable aerosol delivery device is provided. The method includes removably, sealably connecting an adapter of an aerosol delivery device with a corresponding adapter of a container for refilling the aerosol delivery device with aerosol precursor composition, the adapter engaging a valve of the corresponding adapter, and transferring aerosol precursor composition from the container into the aerosol delivery device.

In some example implementations of the method of the preceding or any subsequent example implementation, or any combination thereof the valve includes a valve body that is depressed when the adapter is connected to the corresponding adapter. The valve body may include a first valve member and a second valve member. The first valve member may open a passageway to aerosol precursor composition within the container, and the second valve member may close the airflow port, when the valve body is depressed.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE FIGURES

Figure 1:
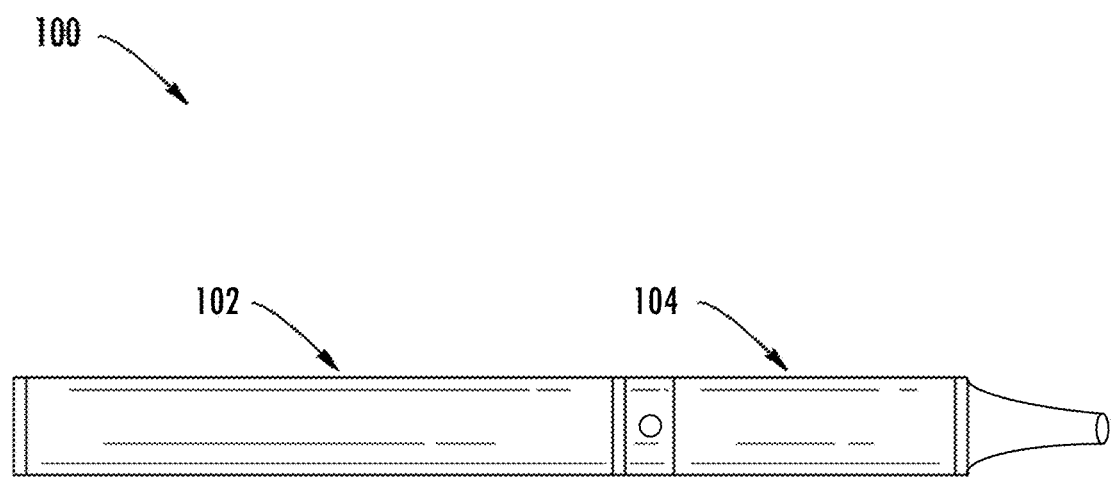
Figure 2:
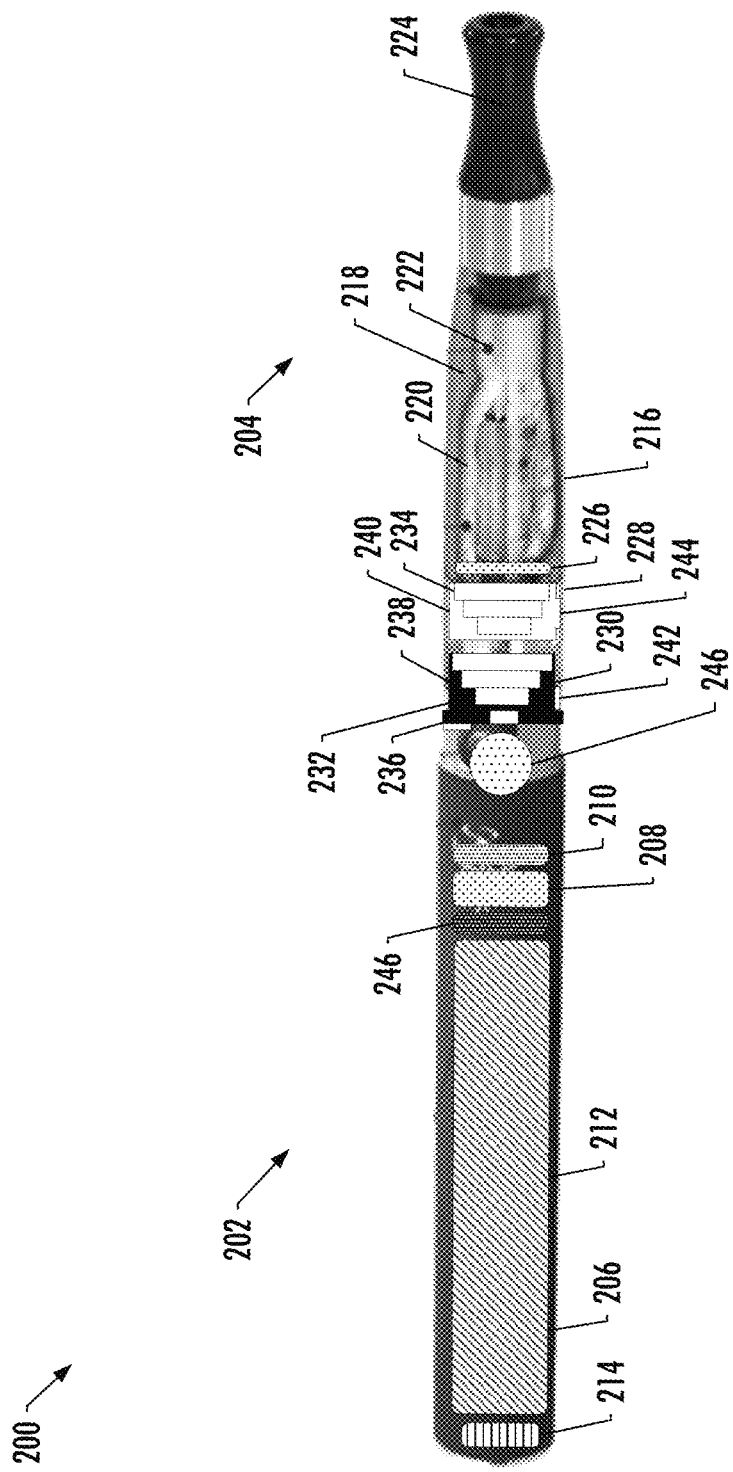
Figure 3:
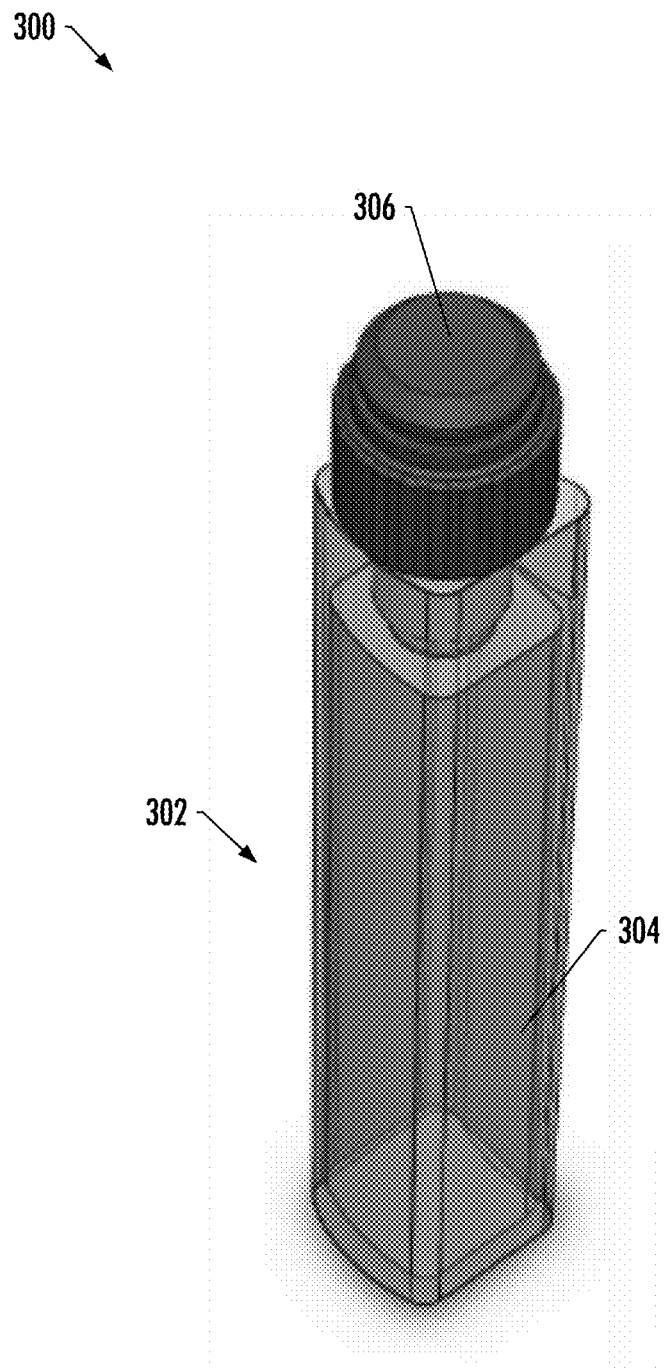
Figure 6:
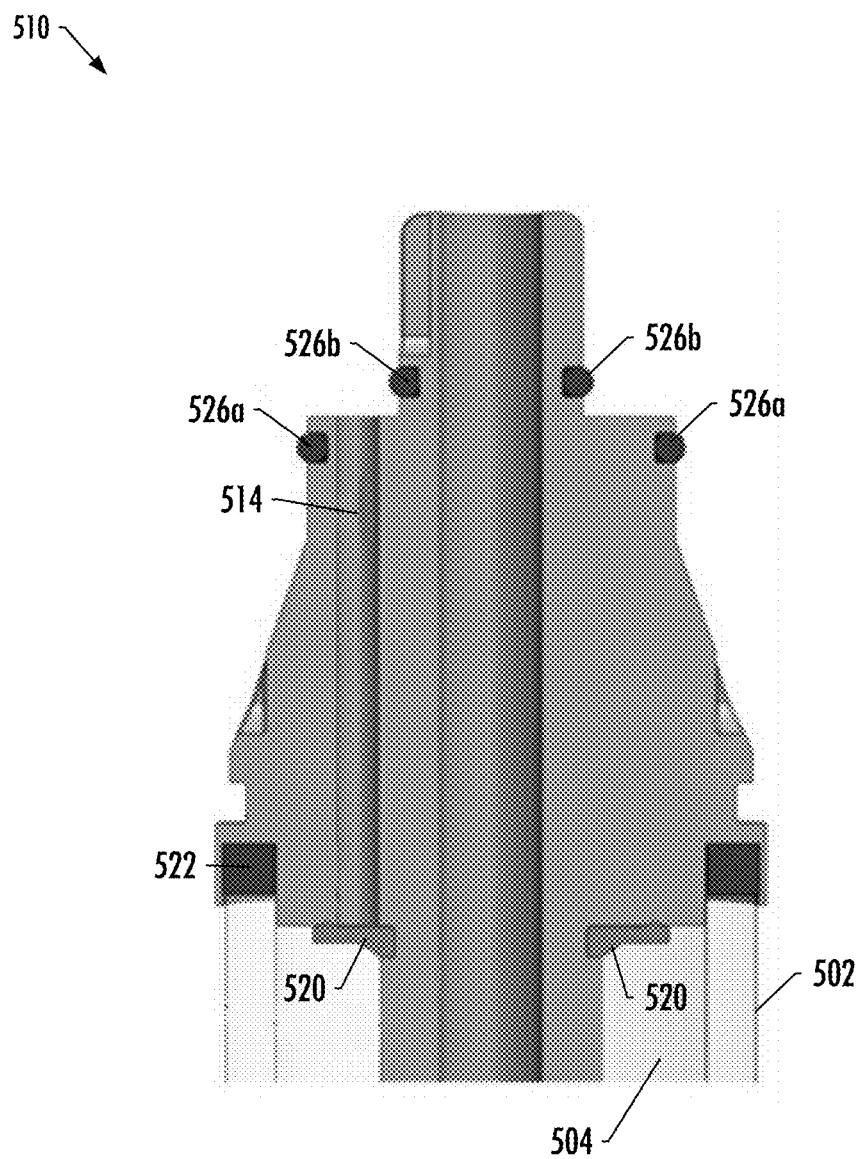
Figures 7A, 7B:
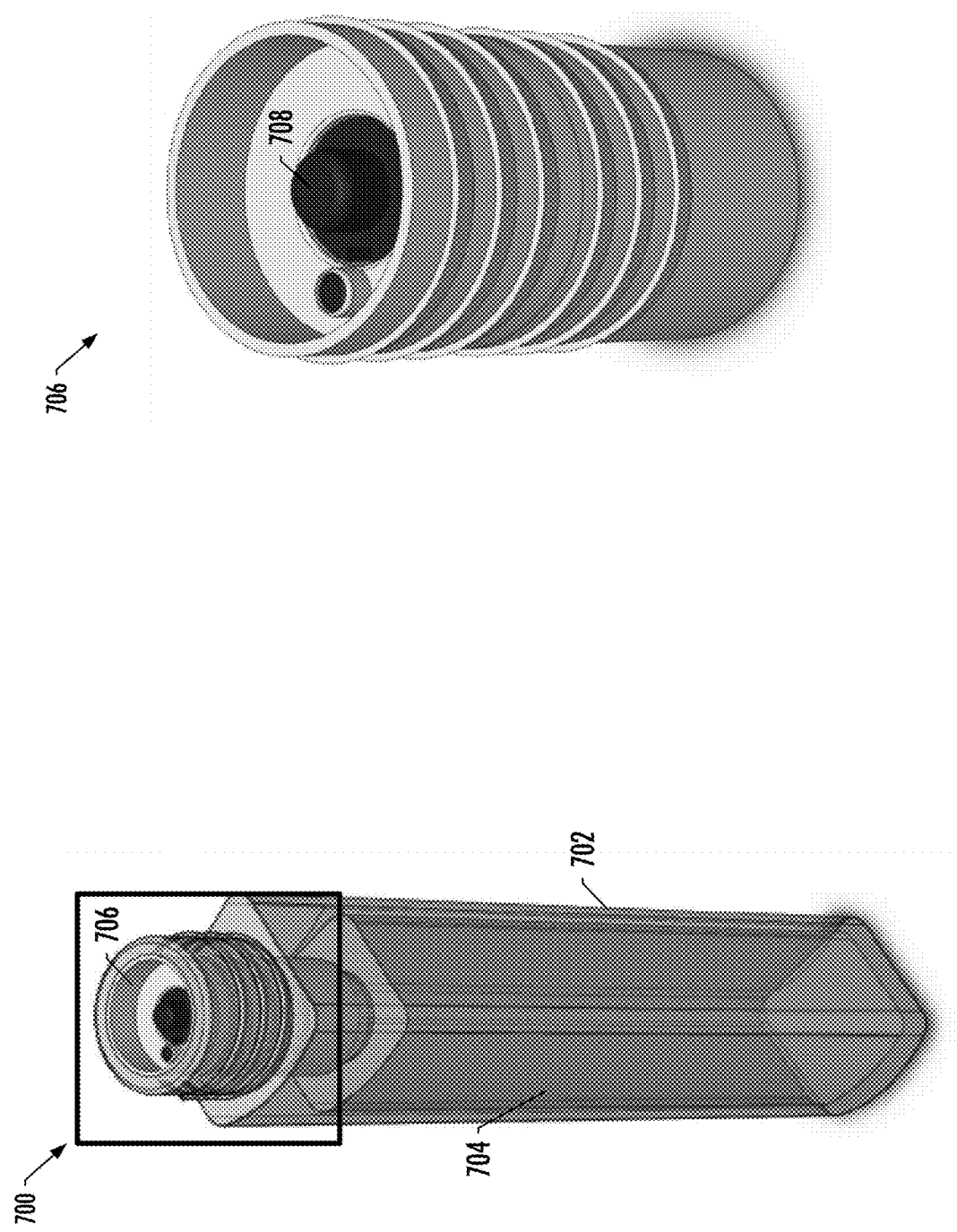
Figure 8B:
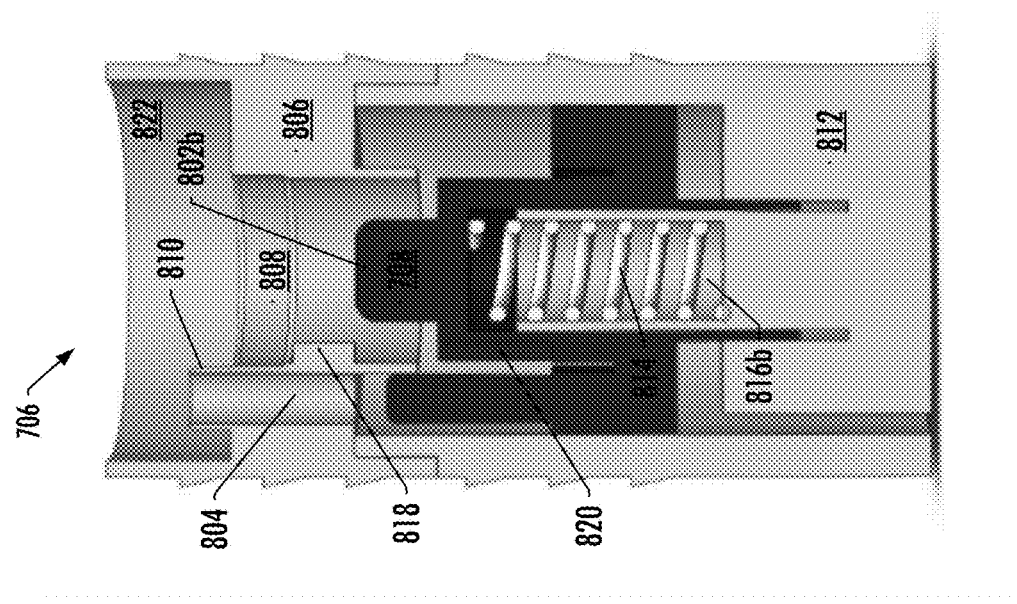
Figure 8A:
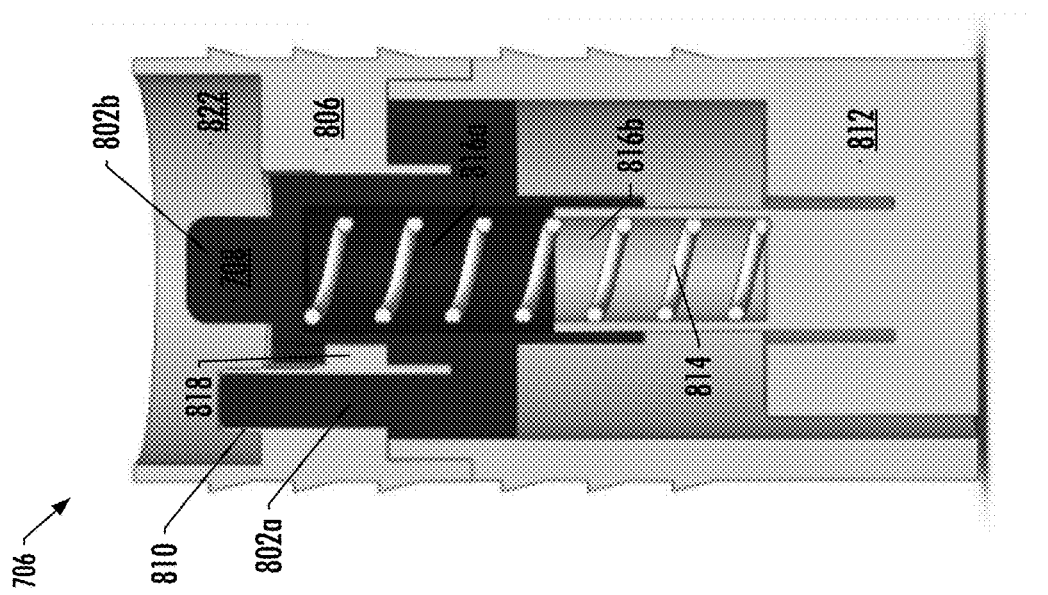
Figure 10:
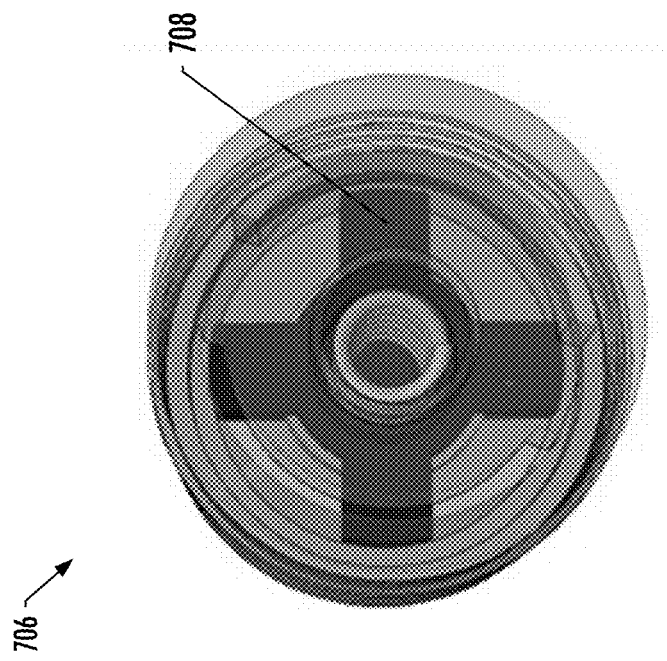
Figure 9:
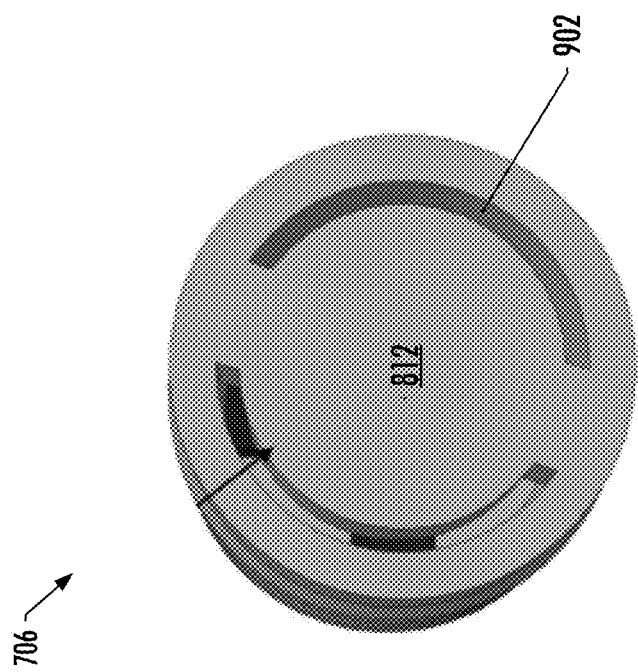
Figure 11:
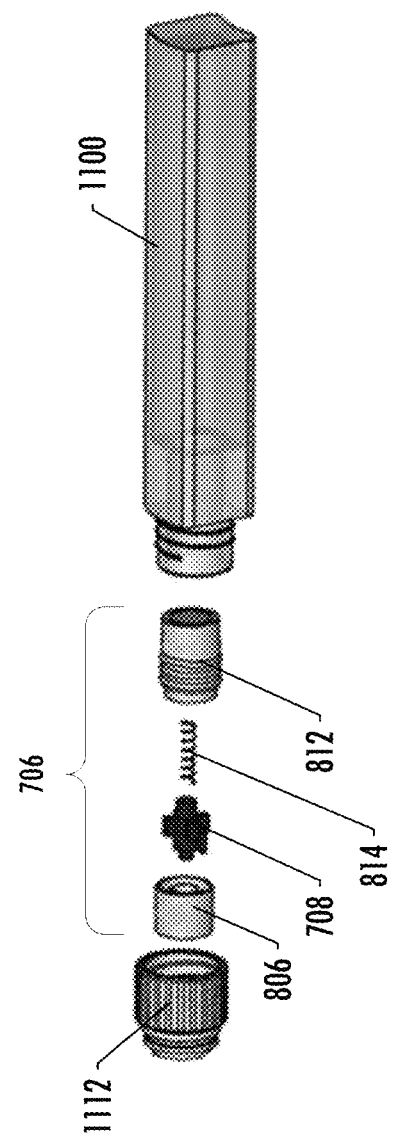
Figure 12:
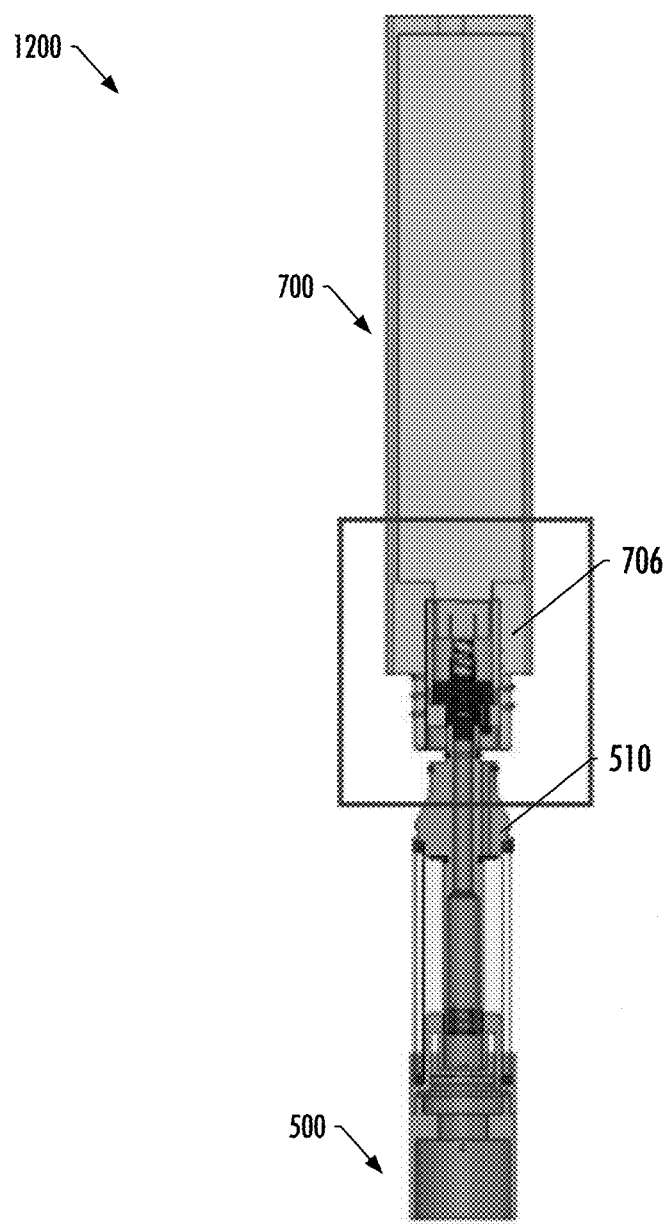
Figure 13B:
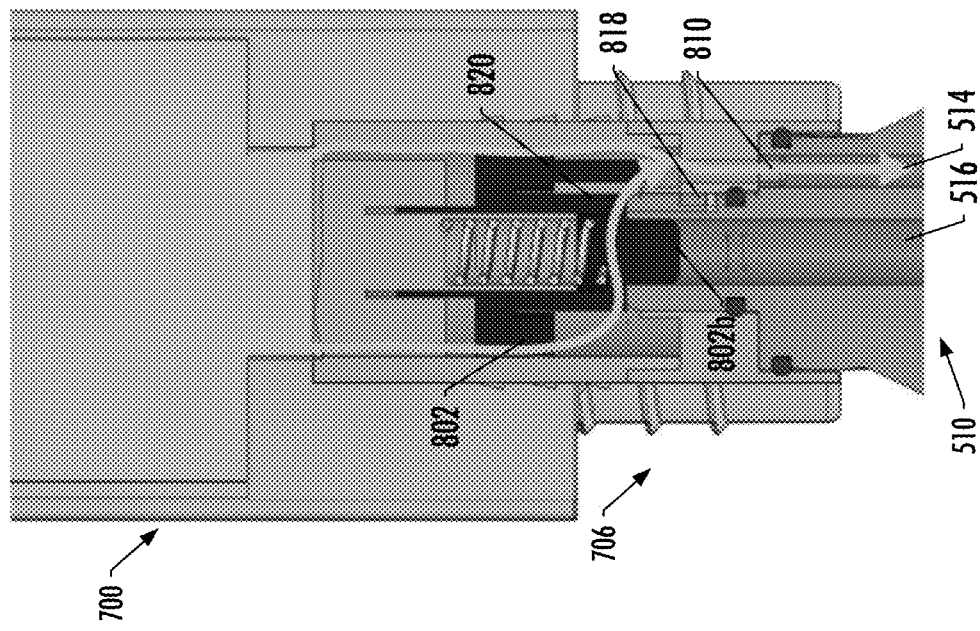
Figure 13A:
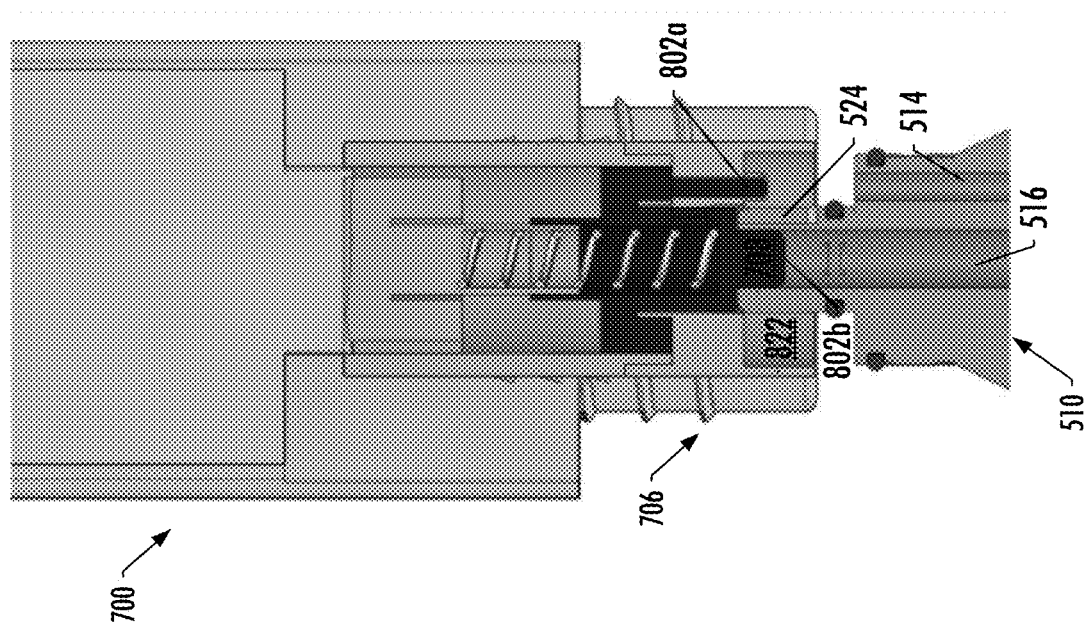

Having thus described the disclosure in the foregoing general terms, reference will now be made to the accompanying drawings, which are not necessarily drawn to scale, and wherein:

FIG. 1 illustrates an aerosol delivery device including a tank coupled to a control body according to an example implementation of the present disclosure;

FIG. 2 is a partially cut-away view of an aerosol delivery device that according to various example implementations may correspond to the aerosol delivery device of FIG. 1;

FIG. 3 illustrates a container of aerosol precursor composition including a reservoir according to an example implementation of the present disclosure;

FIGS. 4A and 4B illustrate an aerosol delivery device including a removal-resistant mouthpiece according to an example implementation of the present disclosure;

FIGS. 5A and 5B illustrate an adapter for receiving an aerosol precursor composition within an aerosol delivery device according to an example implementation of the present disclosure;

FIG. 6 is a partially cut-away view of an adapter for receiving an aerosol precursor composition within an aerosol delivery device that according to various example implementations may correspond to the adapter of FIGS. 4A and 4B;

FIGS. 7A and 7B illustrates an adapter for transferring an aerosol precursor composition from within a container according to an example implementation of the present disclosure;

FIGS. 8A and 8B are a partially cut-away view of an adapter for transferring an aerosol precursor composition from within a container that according to various example implementations may correspond to the adapter of FIGS. 7A and 7B;

FIGS. 9 and 10 are a bottom perspective view of an adapter for transferring an aerosol precursor composition from within a container that according to various example implementations may correspond to the adapter of FIGS. 7A and 7B;

FIG. 11 is an exploded view of a container for refilling aerosol delivery devices including an adapter for transferring an aerosol precursor composition from within a container that according to various example implementations may correspond to the container of FIG. 3 and the adapter of FIGS. 7A and 7B;

FIG. 12 illustrates a contained liquid system for refilling aerosol delivery devices according to an example implementation of the present disclosure;

FIGS. 13A and 13B are a partially cut-away view of a contained liquid system for refilling aerosol delivery devices that according to various example implementations may correspond to the contained liquid system of FIG. 12; and FIG. 14 illustrates various operations in a method for implementing a contained liquid system for use with a refillable aerosol delivery device, according to an example implementation of the present disclosure.

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise.

As described hereinafter, example implementations of the present disclosure relate to aerosol delivery systems. Aerosol delivery systems according to the present disclosure use electrical energy to heat a material (preferably without combusting the material to any significant degree and/or without significant chemical alteration of the material) to form an inhalable substance; and components of such systems have the form of articles that most preferably are sufficiently compact to be considered hand-held devices. That is, use of components of preferred aerosol delivery systems does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery systems of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

Aerosol delivery devices of the present disclosure generally include a number of components provided within an outer body or shell, which may be referred to as a housing. The overall design of the outer body or shell can vary, and the format or configuration of the outer body that can define the overall size and shape of the aerosol delivery device can vary. For some aerosol delivery devices, an elongated body resembling the shape of a cigarette or cigar can be a formed from a single, unitary housing, or the elongated housing can be formed of two or more separable bodies. For example, an aerosol delivery device can comprise an elongated shell or body that can be substantially tubular in shape and, as such, resemble the shape of a conventional cigarette or cigar. In one implementation, all of the components of the aerosol delivery device are contained within a single housing. Alternatively, an aerosol delivery device can comprise two or more housings that are joined and are separable. For example, an aerosol delivery device can possess at one end a control body comprising a housing containing one or more reusable components (e.g., a rechargeable battery and various electronics for controlling the operation of that article), and at the other end and removably attached thereto an outer body or shell containing a portion including one or more aerosol precursor components, such as flavors and aerosol formers. In various implementations, this portion may be a disposable portion (e.g., a disposable cartridge) or a refillable portion (e.g., a refillable tank).

Aerosol delivery devices of the present disclosure can be formed of an outer housing or shell that is not substantially tubular in shape but may be formed to substantially greater dimensions. The housing or shell can be configured to include a mouthpiece and/or may be configured to receive a separate shell (e.g., a cartridge, a tank) that can include consumable elements, such as a liquid aerosol former, and can include a vaporizer.

Aerosol delivery systems of the present disclosure most preferably comprise some combination of a power source (i.e., an electrical power source), at least one control component (e.g., means for actuating, controlling, regulating and ceasing power for heat generation, such as by controlling electrical current flow from the power source to other components of the article—e.g., a microprocessor, individually or as part of a microcontroller), a heater or heat generation member (e.g., an electrical resistance heating element or other component, which alone or in combination with one or more further elements may be commonly referred to as an "atomizer"), an aerosol precursor composition (e.g., commonly a liquid capable of yielding an aerosol upon application of sufficient heat, such as ingredients commonly referred to as "smoke juice," "e-liquid" and "e-juice"), and a mouth end region or tip for allowing draw upon the aerosol delivery device for aerosol inhalation (e.g., a defined airflow path through the article such that aerosol generated can be withdrawn therefrom upon draw).

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

FIG. 1 illustrates a side view of an aerosol delivery device 100 including a control body 102 and a tank 104, according to various example implementations of the present disclosure. In particular, FIG. 1 illustrates the control body and the tank coupled to one another. The control body and the tank may be permanently or detachably aligned in a functioning relationship. Various mechanisms may connect the tank to the control body to result in a threaded engagement, a press-fit engagement, an interference fit, a magnetic engagement or the like. In some examples, the aerosol delivery device may be substantially rod-like, substantially tubular shaped, or substantially cylindrically shaped in some example implementations when the tank and the control body are in an assembled configuration. In other examples, further shapes and dimensions are encompassed—e.g., a rectangular or triangular cross-section, multifaceted shapes, or the like. The tank and control body may include a unitary housing or outer body or separate, respective housings or outer bodies, which may be formed of any of a number of different materials. The housing may be formed of any combination of suitable, structurally-sound materials. In some examples, the housing may be formed of at least one of a metal or alloy, such as stainless steel, aluminum or the like. Other suitable materials include various plastics (e.g., polycarbonate), metal-plating over plastic, glass, and the like.

In some example implementations, one or both of the control body 102 or the tank 104 of the aerosol delivery device 100 may be referred to as being disposable or as being reusable. For example, the control body may have a replaceable battery or a rechargeable battery and thus may be combined with any type of recharging technology, including connection to a typical alternating current electrical outlet, connection to a car charger (i.e., a cigarette lighter receptacle), and connection to a computer, such as through a universal serial bus (USB) cable or connector. For example, an adaptor including a USB connector at one end and a control body connector at an opposing end is disclosed in U.S. Pat. Pub. No. 2014/0261495 to Novak et al., which is incorporated herein by reference in its entirety. Further, in some example implementations, the control body may be coupled to a tank comprising a refillable reservoir therein. The reservoir may be configured to retain the aerosol precursor composition. In some example implementations, the reservoir particularly can be formed of a porous material (e.g., a fibrous material) and thus may be referred to as a porous substrate (e.g., a fibrous substrate).

A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material. In particular examples, a cellulose acetate material can be used. In other example implementations, a carbon material can be used. A reservoir may be substantially in the form of a container and may include a fibrous material included therein. In other implementations, the reservoir may be formed of a glass, plastic, or other materials not explicitly set forth herein.

In one example implementation, the control body 102 and tank 104 forming the aerosol delivery device 100 may be permanently and/or removably coupled to one another. Examples of aerosol delivery devices that may be configured to be disposable and/or which may include first and second outer bodies that are configured for permanent coupling are disclosed in U.S. patent application Ser. No. 14/170,838 to Bless et al., filed Feb. 3, 2014, which is incorporated herein by reference in its entirety. In another example implementation, the tank and control body may be configured in a single-piece, non-detachable form and may incorporate the components, aspects, and features disclosed herein. However, in another example implementation, the control body and tank may be configured to be separable such that, for example, the tank may be refilled or replaced.

FIG. 2 illustrates a more particular example of a suitable aerosol delivery device 200 that in some examples may correspond to the aerosol delivery device 100 of FIG. 1. As seen in the cut-away view illustrated therein, the aerosol delivery device can comprise a control body 202 and a tank 204, which may correspond to respectively the control body 102 and tank 104 of FIG. 1. As illustrated in FIG. 2, the control body 202 can be formed of a control body shell 206 that can include a control component 208 (e.g., a printed circuit board (PCB), an integrated circuit, a memory component, a microprocessor, individually or as part of a microcontroller, and the like), a flow sensor 210, a battery 212, and one or more light-emitting diodes (LEDs) 214, and such components can be variably aligned. Further indicators (e.g., a haptic feedback component, an audio feedback component, or the like) can be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; and U.S. patent application Ser. No. 14/173,266, filed Feb. 5, 2014, to Sears et al.; which are incorporated herein by reference.

The tank 204 can be formed of a tank shell 216 enclosing a reservoir 218 that is in fluid communication with a liquid transport element 220 adapted to wick or otherwise transport an aerosol precursor composition stored in the reservoir housing to a heater 222 (sometimes referred to as a heating element). In some examples, a valve may be positioned between the reservoir and heater, and configured to control an amount of aerosol precursor composition passed or delivered from the reservoir to the heater.

Various examples of materials configured to produce heat when electrical current is applied therethrough may be employed to form the heater 222. The heater in these examples may be resistive heating element such as a coil. Example materials from which the coil may be formed include Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials (e.g., carbon-based foams and yarns) and ceramics (e.g., positive or negative temperature coefficient ceramics). Example implementations of heaters or heating members useful in aerosol delivery devices according to the present disclosure are further described below, and can be incorporated into devices such as illustrated in FIG. 2 as described herein.

A mouthpiece 224 having an opening defined therein may be coupled to the tank shell 216 (e.g., at the mouthend) to allow for egress of formed aerosol from the tank 204. Such components are representative of the components that may be present in a tank and are not intended to limit the scope of tank components that are encompassed by the present disclosure.

The tank 204 also may include one or more electronic components 226, which may include an integrated circuit, a memory component, a sensor, or the like. The electronic components may be adapted to communicate with the control component 208 and/or with an external device by wired or wireless means. The electronic components may be positioned anywhere within the tank or a base 228 thereof.

The control component 208 includes a number of electronic components, and in some examples may be formed of an electronic or printed circuit board (PCB) that supports and electrically connects the electronic components. The electronic components may include a microprocessor or processor core, and a memory. In some examples, the control component may include a microcontroller with integrated processor core and memory, and which may further include one or more integrated input/output peripherals. In some examples, the control component may be coupled to a communication interface to enable wireless communication with one or more networks, computing devices or other appropriately-enabled devices. Examples of suitable communication interfaces are disclosed in U.S. patent application Ser. No. 14/638,562, filed Mar. 4, 2015, to Marion et al., the content of which is incorporated by reference in its entirety. And examples of suitable manners according to which the aerosol delivery device may be configured to wirelessly communicate are disclosed in U.S. patent application Ser. No. 14/327,776, filed Jul. 10, 2014, to Ampolini et al., and U.S. patent application Ser. No. 14/609,032, filed Jan. 29, 2015, to Henry, Jr. et al., each of which is incorporated herein by reference in its entirety.

Although the control component 208 and the flow sensor 210 are illustrated separately, it is understood that the control component and the flow sensor may be combined, such as on a PCB to which the air flow sensor may be directly attached. Further, the PCB may be positioned horizontally relative to the illustration of FIG. 2 in that the PCB can be lengthwise parallel to the central axis of the control body. In some examples, the air flow sensor may comprise its own circuit board or other base element to which it can be attached. In some examples, a flexible circuit board may be utilized. A flexible circuit board may be configured into a variety of shapes, include substantially tubular shapes. In some examples, a flexible circuit board may be combined with, layered onto, or form part or all of a heater substrate as further described below.

The control body 202 and the tank 204 may include components adapted to facilitate a fluid engagement therebetween. As illustrated in FIG. 2, the control body can include a coupler 230 having a cavity 232 therein. The base 228 of the tank can be adapted to engage the coupler and can include a projection 234 adapted to fit within the cavity. Such engagement can facilitate a stable connection between the control body and the tank as well as establish an electrical connection between the battery 212 and control component 208 in the control body and the heater 222 in the tank. Further, the control body shell 206 can include an air intake 236, which may be a notch in the shell where it connects to the coupler that allows for passage of ambient air around the coupler and into the shell where it then passes through the cavity 232 of the coupler and into the tank through the projection 234.

A coupler and a base useful according to the present disclosure are described in U.S. Pat. App. Pub. No. 2014/0261495 to Novak et al., which is incorporated herein by reference in its entirety. For example, the coupler 230 as seen in FIG. 2 may define an outer periphery 238 configured to mate with an inner periphery 240 of the base 228. In one example the inner periphery of the base may define a radius that is substantially equal to, or slightly greater than, a radius of the outer periphery of the coupler. Further, the coupler may define one or more protrusions 242 at the outer periphery configured to engage one or more recesses 244 defined at the inner periphery of the base. However, various other examples of structures, shapes and components may be employed to couple the base to the coupler. In some examples the connection between the base of the tank 204 and the coupler of the control body 202 may be substantially permanent, whereas in other examples the connection therebetween may be releasable such that, for example, the control body may be reused with one or more additional tanks that may be disposable and/or refillable.

The reservoir 218 illustrated in FIG. 2 can be a container or can be a reservoir, as presently described. For example, the reservoir can be substantially formed into the shape of a tube encircling the interior of the tank shell 216, in this example. An aerosol precursor composition can be retained in the reservoir. Liquid components, for example, can be retained by the reservoir. The reservoir can be in fluid connection with the liquid transport element 220. The liquid transport element can transport the aerosol precursor composition stored in the reservoir via capillary action to the heater 222 that is in the form of a metal wire coil in this example. As such, the heater is in a heating arrangement with the liquid transport element. Example implementations of reservoirs and transport elements useful in aerosol delivery devices according to the present disclosure are further described below, and such reservoirs and/or transport elements can be incorporated into devices such as illustrated in FIG. 2 as described herein. In particular, specific combinations of heating members and transport elements as further described below may be incorporated into devices such as illustrated in FIG. 2 as described herein.

In use, when a user draws on the aerosol delivery device 200, airflow is detected by the flow sensor 210, and the heater 222 is activated to vaporize components of the aerosol precursor composition. Drawing upon the mouthpiece 224 of the aerosol delivery device causes ambient air to enter the air intake 236 and pass through the cavity 232 in the coupler 230 and the central opening in the projection 234 of the base 228. In the tank 204, the drawn air combines with the formed vapor to form an aerosol. The aerosol is whisked, aspirated or otherwise drawn away from the heater and out the opening in the mouthpiece of the aerosol delivery device.

An input element 246 may be included with the aerosol delivery device 200. The input element may be included to allow a user to control functions of the device and/or for output of information to a user. For example, a user may utilize the input element to vaporize an aerosol precursor composition and/or activate an on/off function. Any component or combination of components may be utilized as an input for controlling the function of the device. For example, one or more pushbuttons may be used as described in U.S. patent application Ser. No. 14/193,961, filed Feb. 28, 2014, to Worm et al., which is incorporated herein by reference. Likewise, a touchscreen may be used as described in U.S. patent application Ser. No. 14/643,626, filed Mar. 10, 2015, to Sears et al., which is incorporated herein by reference. As a further example, components adapted for gesture recognition based on specified movements of the aerosol delivery device may be used as an input. See U.S. patent application Ser. No. 14/565,137, filed Dec. 9, 2014, to Henry et al., which is incorporated herein by reference.

In some example implementations, a computing device such as a mobile computer (e.g., smartphone, tablet computer) may be used as an input element in addition to or in lieu of an input element 246 on the aerosol delivery device itself. In particular, the aerosol delivery device 200 may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. patent application Ser. No. 14/327,776, filed Jul. 10, 2014, to Ampolini et al., the disclosure of which is incorporated herein by reference. In such implementations, application software may be used in connection with the computing device to input control instructions to the aerosol delivery device, such control instructions including, for example, the ability to form an aerosol of specific composition by choosing the nicotine content and/or content of further flavors to be included.

In some examples, the aerosol delivery device 200 may include a number of additional hardware-implemented or software-controlled functions. For example, the aerosol delivery device may include a battery protection circuit configured to detect battery input, loads on the battery terminals, and charging input. The battery protection circuit may include short-circuit protection and under-voltage lock out. The aerosol delivery device may also include components for ambient temperature measurement, and its control component 208 may be configured to control at least one functional element to inhibit battery charging if the ambient temperature is below a certain temperature (e.g., 0° C.) or above a certain temperature (e.g., 45° C.) prior to start of charging or during charging.

Power delivery from the battery 212 may vary over the course of each puff on the device 200 according to a power control mechanism. The device may include a "long puff" safety timer such that in the event that a user or an inadvertent mechanism causes the device to attempt to puff continuously, the control component 208 may control at least one functional element to terminate the puff automatically after some period of time (e.g., four seconds). Further, the time between puffs on the device may be restricted to less than a period of time (e.g., 100). A watchdog safety timer may automatically reset the aerosol delivery device if its control component or software running on it becomes unstable and does not service the timer within an appropriate time interval (e.g., eight seconds). Further safety protection may be provided in the event of a defective or otherwise failed flow sensor 210, such as by permanently disabling the aerosol delivery device in order to prevent inadvertent heating. A puffing limit switch may deactivate the device in the event of a pressure sensor fail causing the device to continuously activate without stopping after the four second maximum puff time.

The aerosol delivery device 200 may include a puff tracking algorithm configured for heater lockout once a defined number of puffs has been achieved for an attached tank (based on the number of available puffs calculated in light of the e-liquid charge in the tank). In some implementations, the puff tracking algorithm indirectly counts the number of puffs based on a corresponding number of puff seconds. As such, the puff tracking algorithm may incrementally count a number of puff seconds in order to calculate when a specified number of puffs have occurred and subsequently shut off the device once the puff seconds reach what is estimated to be a pre-determined number of puffs. For example, if three (3) seconds is defined to be equivalent to one "average" puff and the device have been configured to shut down after two hundred (200) average puffs, the device may shut down after six hundred (600) puff second have elapsed with respect to usage of the tank. The puff tracking algorithm may further estimate the amount of e-liquid that is utilized per puff second, and mathematically calculate the e-liquid volume based at least in part on the estimation of corresponding puffs seconds.

The aerosol delivery device 200 may include a sleep, standby or low-power mode function whereby power delivery may be automatically cut off after a defined period of non-use. Further safety protection may be provided in that all charge/discharge cycles of the battery 212 may be monitored by the control component 208 over its lifetime. After the battery has attained the equivalent of a predetermined number (e.g., 200) full discharge and full recharge cycles, it may be declared depleted, and the control component may control at least one functional element to prevent further charging of the battery.

The various components of an aerosol delivery device according to the present disclosure can be chosen from components described in the art and commercially available. Examples of batteries that can be used according to the disclosure are described in U.S. Pat. Pub. No. 2010/0028766 to Peckerar et al., the disclosure of which is incorporated herein by reference in its entirety.

The aerosol delivery device 200 can incorporate the sensor 210 or another sensor or detector for control of supply of electric power to the heater 222 when aerosol generation is desired (e.g., upon draw during use). As such, for example, there is provided a manner or method of turning off the power supply to the heater when the aerosol delivery device is not be drawn upon during use, and for turning on the power supply to actuate or trigger the generation of heat by the heater during draw. Additional representative types of sensing or detection mechanisms, structure and configuration thereof, components thereof, and general methods of operation thereof, are described in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference in their entireties.

The aerosol delivery device 200 most preferably incorporates the control component 208 or another control mechanism for controlling the amount of electric power to the heater 222 during draw. Representative types of electronic components, structure and configuration thereof, features thereof, and general methods of operation thereof, are described in U.S. Pat. No. 4,735,217 to Gerth et al., U.S. Pat. No. 4,947,874 to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. App. Pub. No. 2009/0230117 to Fernando et al., U.S. Pat. App. Pub. No. 2014/0060554 to Collet et al., U.S. Pat. App. Pub. No. 2014/0270727 to Ampolini et al., and U.S. patent application Ser. No. 14/209, 191 to Henry et al., filed Mar. 13, 2014, all of which are incorporated herein by reference in their entireties.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. patent application Ser. No. 14/011,992 to Davis et al., filed Aug. 28, 2013, and U.S. patent application Ser. No. 14/170,838 to Bless et al., filed Feb. 3, 2014, all of which are incorporated herein by reference in their entireties. Additionally, various wicking materials, and the configuration and operation of those wicking materials within certain types of electronic cigarettes, are set forth in U.S. Pat. App. Pub. No. 2014/0209105 to Sears et al., which is incorporated herein by reference in its entirety.

For aerosol delivery systems that are characterized as electronic cigarettes, the aerosol precursor composition most preferably incorporates tobacco or components derived from tobacco. In one regard, the tobacco may be provided as parts or pieces of tobacco, such as finely ground, milled or powdered tobacco lamina. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

The aerosol precursor composition, also referred to as a vapor precursor composition, may comprise a variety of components including, by way of example, a polyhydric alcohol (e.g., glycerin, propylene glycol, or a mixture thereof), nicotine, tobacco, tobacco extract, and/or flavorants. Various components that may be included in the aerosol precursor composition are described in U.S. Pat. No. 7,726,320 to Robinson et al., which is incorporated herein by reference in its entirety. Additional representative types of aerosol precursor compositions are set forth in U.S. Pat. No. 4,793,365 to Sensabaugh, Jr. et al., U.S. Pat. No. 5,101,839 to Jakob et al., U.S. Pat. No. 6,779,531 to Biggs et al., U.S. Pat. App. Pub. No. 2013/0008457 to Zheng et al., and *Chemical and Biological Studies on New Cigarette Prototypes that Heat Instead of Burn Tobacco*, R. J. Reynolds Tobacco Company Monograph (1988), all of which are incorporated herein by reference in their entireties.

Representative types of aerosol precursor components and formulations also are set forth and characterized in U.S. Pat. No. 7,217,320 to Robinson et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU™ product by Lorillard Technologies, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. Typically, the amount of aerosol precursor incorporated within the aerosol delivery system, and particularly within the aerosol generating piece, is less than about 2 g, generally less than about 1.5 g, often less than about 1 g and frequently less than about 0.5 g.

Additional representative types of components that yield visual cues or indicators may be employed in the aerosol delivery device 200, such as LEDs and related components, auditory elements (e.g., speakers), vibratory elements (e.g., vibration motors) and the like. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. patent application Ser. No. 14/173,266 to Sears et al., filed Feb. 5, 2014, all of which are incorporated herein by reference in their entireties.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. App. Pub. No. 2010/0163063 to Fernando et al., U.S. Pat. App. Pub. No. 2013/0192623 to Tucker et al., U.S. Pat. App. Pub. No. 2013/0298905 to Leven et al., U.S. Pat. App. Pub. No. 2013/0180553 to Kim et al., U.S. Pat. App. Pub. No. 2014/0000638 to Sebastian et al., U.S. Pat. App. Pub. No. 2014/0261495 to Novak et al., and U.S. Pat. App. Pub. No. 2014/0261408 to DePiano et al., all of which are incorporated herein by reference in their entireties.

As previously explained, the tank 204 can be formed of a tank shell 216 enclosing a reservoir 218 therein. In some example implementations, the reservoir may be a refillable reservoir, and a container of aerosol precursor composition may be provided for refilling the reservoir. The tank and container may be removably, sealably connectable to one another such that the sealed coupling between the tank and the container may be configured to safely enable the transfer of aerosol precursor composition between the container and the aerosol delivery device.

FIG. 3 illustrates a perspective view of a container 300 of aerosol precursor composition, according to various example implementations of the present disclosure. As shown, the container includes a container shell 302 that may comprise a reservoir 304 configured to contain an aerosol precursor composition, and a cap 306 that may be configured to cover a passageway to the reservoir. In particular, FIG. 3 illustrates the container shell and the cap coupled to one another. The container shell and the cap may be removably coupled to one another. Various mechanisms may connect the container shell to the cap to result in a threaded engagement, a press-fit engagement, an interference fit, a magnetic engagement or the like. In some examples, the container may be substantially rod-like, substantially tubular shaped, or substantially cylindrically shaped. In other examples, further shapes and dimensions are encompassed—e.g., a rectangular or triangular cross-section, multifaceted shapes, or the like.

The container 300 may be formed of any of a number of different materials. The container shell 302 and cap 306 may be formed of any combination of suitable, structurally-sound materials, and may be formed of the same or different materials. In some examples, the container shell and cap may be formed of at least one of a metal or alloy, such as stainless steel, aluminum or the like. Other suitable materials include various plastics (e.g., polycarbonate), metal-plating over plastic, glass, and the like.

FIGS. 4A and 4B (collectively FIG. 4) illustrate a portion of a tank 400 of an aerosol delivery device that in some examples may correspond to the tank 104 of FIG. 1 (one example of which may be tank 204 of FIG. 2). As shown, the tank may include a tank shell 402, reservoir 404, heater 406 and mouthpiece 408 that may correspond to respective ones of the tank shell 216, reservoir 218, heater 222 and mouthpiece 224 of the tank 204 of FIG. 2. As more particularly shown in FIG. 4, the mouthpiece 408 may be removably coupled to the tank 400 over an adapter 410 (aerosol delivery device adapter) coupled to the tank shell (housing) and removably, sealably connectable with a container of aerosol precursor composition (e.g., container 300) for safely refilling the reservoir with aerosol precursor composition. In this regard, the mouthpiece may be removably coupled to the tank shell (housing), and/or the aerosol delivery device adapter that is in turn coupled to the tank shell. As shown between FIGS. 4A and 4B, the mouthpiece may be positioned over the aerosol delivery device adapter such that the adapter is exposed upon removal of the mouthpiece. In some examples, the mouthpiece may be a removal-resistant mouthpiece including two tabs 408a, 408b the simultaneous pressing of which allows the removal-resistant mouthpiece to turn and thereby release from the tank shell for removal.

The aerosol delivery device adapter 410 may be adapted to removably, sealably connect with a suitable container of aerosol precursor composition (e.g., container 300) in any of a number of different manners. FIGS. 5A and 5B (collectively FIG. 5) illustrate a portion of a tank 500 similar to the tank 400 of FIG. 4 (and that may correspond to tank 104, 204), but further highlighting one example of a suitable aerosol delivery device adapter 510 that may in some examples correspond to the aerosol delivery device adapter 410 of FIG. 4. The tank 500 of FIG. 5 may include a tank shell 502, reservoir 504 and heater 506 that may correspond to respective ones of the tank shell 402, reservoir 404 and heater 406 of the tank 400 of FIG. 4.

As shown in FIG. 5B, the aerosol delivery device adapter 510 may include a body 512 having a filling port 514 and a separate and distinct airflow port 516 defined therein. As used herein, a port may refer to a narrow and elongated passageway through which liquid, air, and the like may be transported. As illustrated, in one example implementation, the ports may be substantially cylindrically shaped so as to allow for the smooth transfer of liquid and/or air. In other example implementations, further shapes and dimensions may be encompassed—e.g., a rectangular or triangular cross-section, multifaceted shapes, or the like.

The filling port 514 may be for transfer of aerosol precursor composition from the container (e.g., container 300) into the reservoir 504 of the aerosol delivery device tank 500 during engagement of the aerosol delivery device adapter and the container. The airflow port 516 may be for the flow of air through at least the portion of the housing of the aerosol delivery device when the aerosol delivery device adapter and the container are disengaged, such as during use of the aerosol delivery device.

As indicated above, in some examples, the aerosol delivery device adapter 510 may be positioned underneath a mouthpiece (e.g., mouthpiece 408) of the aerosol delivery device, and the mouthpiece may be removably coupled to the aerosol delivery device such that the aerosol delivery device adapter is exposed upon removal of the mouthpiece. In some examples, the body 512 of the aerosol delivery device adapter may include an adapter protrusion 518 in which the airflow port 516 may be defined. The adapter protrusion may be positioned beneath the mouthpiece when the mouthpiece is coupled to the aerosol delivery device. Upon removal of the mouthpiece for refilling the reservoir 504, the adapter protrusion may be brought into direct engagement with at least a portion of a container of aerosol precursor composition such that the aerosol delivery device and the container mate with one another.

FIG. 6 illustrates a partially cut-away view of the aerosol delivery device adapter 510 of FIG. 5. As shown, the aerosol delivery device adapter may further include a check valve 520 coupled to the filling port 514. The check valve may allow the transfer of aerosol precursor composition from a container of aerosol precursor composition into the reservoir 504. In particular, the check valve may restrict aerosol precursor composition from flowing out of the reservoir into the filling port. In this way, aerosol precursor composition may only enter the filling port in one direction. The aerosol delivery device adapter may also include a seal 522 between the aerosol delivery device adapter and the tank shell 502 for sealing the connection between the base of the adapter and the opening of the tank shell. The seal may be formed of any combination of suitable, structurally-sound materials. In some examples, the seal may be formed of at least one of a gasket material, elastomeric material, or the like.

FIG. 7A illustrates a container 700 of aerosol precursor composition that in some examples may correspond to the container 300 of FIG. 3. The container includes a container shell 702 (e.g., container shell 302) that may comprise a reservoir 704 (e.g., container reservoir 304) configured to contain an aerosol precursor composition. The container illustrated in FIG. 7A highlights an adapter 706 (container adapter), further illustrated in FIG. 7B, for transferring an aerosol precursor composition from within the container. The container adapter may be coupled to an opening in the container shell. As such, the container adapter may be shaped and sized to match the opening of the container shell. The container adapter may be configured to be removably and sealably connectable with an aerosol delivery device (e.g., aerosol delivery device 100, 200) for refilling the aerosol delivery device with aerosol precursor composition. As shown in FIG. 7B, the container adapter may include a valve 708 for engaging the aerosol delivery device, and more specifically for engaging the aerosol delivery device adapter during refilling of the aerosol delivery device.

FIGS. 8A and 8B illustrate a partially cut-away view of the container adapter 706 of FIGS. 7A and 7B (collectively FIG. 7). As shown, the valve 708 may be defined by a depressible body including a first valve member 802a and a second valve member 802b. The first valve member may open or close a passageway 804 to aerosol precursor composition stored within the container. In particular, the first valve member may include a projection that is sized to fit and/or sealably engage the passageway thereby further restricting the release of aerosol precursor composition from the reservoir when the valve is not depressed during engagement with the aerosol delivery device.

The second valve member may close an airflow port (e.g., airflow port 516) of the aerosol delivery device when the valve is depressed during engagement with the aerosol delivery device. The container adapter 706 may include a nozzle 806 having a cavity 808 defined therein, in which at least a portion of the valve 708 may be movably positioned within the cavity. The cavity may be sized to receive at least portion of the first valve member when the aerosol delivery device adapter and container adapter are disengaged. The nozzle may include a spout 810 for transferring aerosol precursor composition from the container into the reservoir in which the spout may extend from the passageway.

The adapter 706 may further include a nozzle housing 812 configured to engage the nozzle 806 and house at least a portion of the valve 708 therein such that the valve is movably positioned between the nozzle and the nozzle housing. The nozzle housing may be coupled with the valve via a spring 814 in which the spring may be configured to compress when the valve is depressed and extend when the valve is not depressed. The spring may be positioned within a spring cavity 816$a$ of the nozzle and a spring cavity 816$b$ of the nozzle housing. The nozzle may be positioned over the valve within at least a portion of the nozzle housing such that a sealed connection is provided between the nozzle and the nozzle housing.

FIGS. 9 and 10 illustrate a bottom perspective view of the container adapter 706 of FIGS. 7A-8B. As shown in FIG. 9, the nozzle housing 812 may define one or more liquid ports 902 for allowing aerosol precursor composition to pass from the container reservoir through the bottom of the nozzle. The base of the valve may be shaped such that it allows for fluid engagement between the reservoir of the container (e.g., container reservoir 704) and the interior of the nozzle such that the aerosol precursor composition to pass from the container reservoir through the bottom of the nozzle. As shown in FIG. 10, in some example implementations, the base of the valve 708 may be cross-shaped so as to allow the passage of aerosol precursor composition throughout the cavity 808 of the nozzle 806.

FIG. 11 illustrates an exploded view of a container 1100 for refilling aerosol delivery devices that may be one example of the container 300 of FIG. 3. The container may include and/or be coupled with the container adapter 706 of FIG. 7 including the nozzle 806, valve 708, nozzle housing 812, and spring 814. The nozzle housing 812 may be coupled to an opening of the container housing. The exteriors of the nozzle and the nozzle housing may be threaded so as to allow for a secure and sealed connection between the container and the adapter. In some implementations, the nozzle and nozzle housing may be threaded using ego and/or "510" threading patterns.

In some example implementations, the container 1100 may include a cap 1112 (e.g., cap 304). The cap may be removably coupled to the housing of the container and positioned over the container adapter such that the adapter is exposed upon removal of the cap. In one example implementation, the cap may be a removal-resistant cap including two tabs in which the simultaneous pressing of the tabs allows the removal-resistant cap to turn and thereby enable its removal from the housing of the container. In other implementations, the cap may be a removal-resistant cap configured to remove from the housing via one or more other secured removal method not explicitly contemplated herein. For example, the cap may be configured to remove from the container housing in response to simultaneously applying a downward pressure and turning the cap in a counter-clockwise direction.

FIG. 12 illustrates a contained liquid system 1200 for refilling aerosol delivery devices including the portion of a tank 500 having an aerosol delivery device adapter 510 thereon, and the container of aerosol precursor composition 700 having a container adapter 706 thereon. In such an implementation, the contained liquid system may be configured to safely enable the transfer of an aerosol precursor composition between the container and the aerosol delivery device by creating a sealable connection between the two adapters 510, 706. The adapters may be sized and shaped such that they are configured to mate with one another. In one example implementation, the adapters may be further configured to mate with one another based on radio frequency identification (RFID) technology.

FIGS. 13A and 13B further illustrate the contained liquid system 1200 of FIG. 12. As shown in FIG. 13A, the aerosol precursor composition may be restricted from being transferred until the adapters 510, 706 have completely engaged one another. A complete engagement between the adapters may refer to an operative coupling in which the passage of aerosol precursor composition from the container to the aerosol delivery device is allowed. As shown in FIG. 13B, upon complete engagement of the adapters, a sealable connection may be formed between the aerosol delivery device and the container 700 such that the aerosol precursor composition may be safely transferred from the container into the aerosol delivery device through one or more ports and/or passageways 514, 804.

In some example implementations, the aerosol delivery device adapter 510 may be configured to engage the valve 708 of the container adapter 706 during refilling of the aerosol delivery device tank reservoir 504. The filling port 514 may be configured to transfer aerosol precursor composition received from the container 700 into the reservoir of the aerosol delivery device tank during engagement of the aerosol delivery device adapter and the valve. The filling port 514 may be sized to receive the spout 810 when the aerosol delivery device adapter and the valve are completely engaged.

During engagement of the aerosol delivery device adapter 510 and the container adapter 706 for refilling the reservoir, the airflow port 516 may be closed to prevent the aerosol precursor composition from passing through the airflow port. As previously indicated, the airflow port may be closed by the valve 708 of the container adapter during engagement of the aerosol delivery device and the container adapter. In particular, the airflow port may define an inner cavity sized to receive therein at least a matching portion of a second valve member 802$b$ of the valve. The second valve member may engage and close the airflow port when the body of the valve is depressed.

In some example implementations, the aerosol delivery device adapter 510 and the container adapter 706 may include one or more interface features. As shown in FIG. 5, for example, the aerosol delivery device adapter may include a slot 524 mateable with a matching tab 818 of the container 700 to align the aerosol delivery device adapter with the container for connection therewith. In particular, the tab may align the filling port 514 and the spout 810 to ensure proper engagement between the respective adapters. Similarly, the second valve member 802$b$ may comprise a slot 820 mateable with the matching tab 818 such that the valve 708 may be movably positioned within the valve cavity 808 around the tab. The cavity 808 of the container adapter may be sized to receive the aerosol delivery device adapter protrusion 518 when the aerosol delivery device adapter and container adapter are engaged.

The aerosol delivery device adapter may further include one or more seals 526$a$, 526$b$ to secure the connection between the aerosol delivery device adapter and the container adapter. In particular, a first seal 526a may be positioned around the perimeter of the adapter such that it provides a seal between the nozzle cavity 822 and the aerosol delivery device adapter during engagement with the container adapter. Similarly, the second seal 526b may be positioned around the perimeter of the adapter (beneath the slot 524) such that it provides a seal between the valve cavity 808 and the aerosol delivery device adapter during engagement with the container adapter.

FIG. 14 illustrates various operations in a method 1400 for implementing a contained liquid system for use with a refillable aerosol delivery device according to an example implementation of the present disclosure. As shown in block 1402, the method may include removably, sealably connecting an adapter of an aerosol delivery device with a corresponding adapter of a container of aerosol precursor composition in which the adapter may engage a valve of the corresponding adapter. The adapter may include a body defining separate and distinct filling airflow ports in which the filling port may be configured for transferring aerosol precursor composition from the container into the aerosol delivery device during engagement of the adapter and valve. The airflow port may be closed by the valve to prevent the aerosol precursor composition from passing through the airflow port. The airflow port may also be configured for allowing a flow of air through at least the portion of the aerosol delivery device when the adapter and valve are disengaged. As shown at block 1404, the method may also include transferring aerosol precursor composition from the container into the aerosol delivery device.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIG. 1-13B or as otherwise described above may be included in an aerosol delivery device according to the present disclosure.

Many modifications and other implementations of the disclosure set forth herein will come to mind to one skilled in the art to which these disclosure pertain having the benefit of the teachings presented in the foregoing descriptions and the associated drawings. Therefore, it is to be understood that the disclosure are not to be limited to the specific implementations disclosed and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. A container for refilling an aerosol delivery device comprising:

a housing defining a reservoir for storing an aerosol precursor composition; and an adapter coupled to the housing and removably, sealably connectable with an aerosol delivery device to enable refilling the aerosol delivery device with aerosol precursor composition, the adapter including a valve configured to engage the aerosol delivery device during refilling of the aerosol delivery device, the aerosol delivery device defining separate and distinct filling and airflow ports, the filling port being for transfer of aerosol precursor composition from the reservoir into the aerosol delivery device during engagement of the valve and the aerosol delivery device in which the airflow port is closed by the valve to prevent the aerosol precursor composition from passing through the airflow port, the airflow port being for a flow of air through at least the portion of the aerosol delivery device when the valve and aerosol delivery device are disengaged;

wherein the valve includes a depressible valve body including at least a first valve member for opening and closing a passageway through which aerosol precursor composition flows from the reservoir to the aerosol delivery device, wherein the first valve member includes a projection that is sized to sealably engage the passageway when the valve is not depressed, thereby preventing flow of aerosol precursor composition through the passageway.

2. The container of claim 1, wherein the depressible valve body further includes a second valve member for closing the airflow port, when the valve body is depressed; and wherein the first valve member is further configured to open the passageway to the aerosol precursor composition when the valve body is depressed.

3. The container of claim 2, wherein the airflow port defines an inner cavity, and the second valve member includes a matching portion, the inner cavity being sized to receive therein at least the matching portion of the second valve member.

4. The container of claim 1, wherein the aerosol delivery device includes an adapter protrusion defining the airflow port, and the adapter includes a nozzle within which the valve is movably positioned, the nozzle including a cavity sized to receive therein the at least portion of the valve when the adapter and aerosol delivery device are disengaged, and the adapter protrusion when the adapter and aerosol delivery device are engaged.

5. The container of claim 4, wherein the nozzle includes a spout for transfer of aerosol precursor composition from the reservoir into the aerosol delivery device, and the filling port is sized to receive the spout when the adapter and valve are engaged.

6. The container of claim 4, wherein the nozzle defines one or more liquid ports configured to allow the transfer of aerosol precursor composition from the reservoir into the aerosol delivery device.

7. The container of claim 1 further comprising a cap removably coupled to the housing over the adapter such that the adapter is exposed upon removal of the cap.

8. The container of claim 7, wherein the cap is a removal-resistant cap including two tabs the simultaneous pressing of which allows the removal-resistant cap to turn and thereby its removal from the housing.

9. The container of claim 1 wherein the adapter further includes a tab mateable with a matching slot of the aerosol delivery device to align the adapter with the aerosol delivery device for connection therewith.

10. A method for implementing a contained liquid system for use with a refillable aerosol delivery device, the method comprising:

removably, sealably connecting an adapter of an aerosol delivery device with the adapter of the container of claim 1 for refilling the aerosol delivery device with aerosol precursor composition, the adapter of the aerosol delivery device engaging the valve of the adapter of the container, the adapter of the aerosol delivery device including a body defining separate and distinct filling airflow ports, the filling port being for transfer of aerosol precursor composition from the container into the aerosol delivery device during engagement of the adapter of the aerosol delivery device and the valve in which the airflow port is closed by the valve to prevent the aerosol precursor composition from passing through the airflow port, the airflow port being for a flow of air through at least the portion of the aerosol delivery device when the adapter of the aerosol delivery device and valve are disengaged; and transferring aerosol precursor composition from the container into the aerosol delivery device, wherein the valve includes a depressible valve body including at least a first valve member for opening and closing a passageway through which aerosol precursor composition flows from the reservoir to the aerosol delivery device, wherein the first valve member includes a projection that is sized to sealably engage the passageway when the valve is not depressed, thereby preventing flow of aerosol precursor composition through the passageway.

11. The method of claim 10, wherein the depressible valve body further includes a second valve member for closing the airflow port, when the valve body is depressed; and wherein the first valve member is further configured to open the passageway to the aerosol precursor composition when the valve body is depressed.

* * * * *